(12) United States Patent
Luo

(10) Patent No.: US 12,350,430 B2
(45) Date of Patent: Jul. 8, 2025

(54) RESPIRATORY MASK WITH GOOD SEALING AND COMFORT

(71) Applicant: DCSTAR INC., New York, NY (US)

(72) Inventor: David Luo, New York, NY (US)

(73) Assignee: DCSTAR INC, New York, NY (US)

( * ) Notice: Subject to any disclaimer, the term of this patent is extended or adjusted under 35 U.S.C. 154(b) by 0 days.

(21) Appl. No.: 18/509,922

(22) Filed: Nov. 15, 2023

(65) Prior Publication Data

US 2025/0152887 A1    May 15, 2025

(51) Int. Cl.
*A61M 16/06* (2006.01)
(52) U.S. Cl.
CPC ..... *A61M 16/0622* (2014.02); *A61M 2207/10* (2013.01)
(58) Field of Classification Search
CPC .......... A61M 16/0622; A61M 2207/10; A61M 16/06–0694
See application file for complete search history.

(56) References Cited

U.S. PATENT DOCUMENTS

| 2009/0014007 A1* | 1/2009 | Brambilla | A61M 16/0616 |
| | | | 128/206.24 |
| 2010/0326445 A1* | 12/2010 | Veliss | A61M 16/106 |
| | | | 128/206.24 |
| 2014/0251338 A1* | 9/2014 | Asvadi | C08G 77/392 |
| | | | 128/206.22 |
| 2015/0246198 A1* | 9/2015 | Bearne | A61M 16/06 |
| | | | 128/205.25 |
| 2017/0128689 A1* | 5/2017 | Law | A61M 16/0683 |
| 2020/0016358 A1* | 1/2020 | Bornholdt | A61M 16/0069 |
| 2023/0302245 A1* | 9/2023 | Eves | A61M 16/0683 |

FOREIGN PATENT DOCUMENTS

WO   WO-2014117227 A9 * 10/2014   ........ A61M 16/0069

* cited by examiner

*Primary Examiner* — Valerie L Woodward
(74) *Attorney, Agent, or Firm* — HSML P.C.

(57) ABSTRACT

A comfortable, well-sealing respiratory mask with an annular comfort layer. The respiratory mask includes a rigid component, an elastic component, and an annular comfort layer. The rigid component is equipped with a gas delivery interface and an annular interface; the elastic component is connected to the rigid component and features a first accommodation area designed to house the user's mouth and nose or only the nose. On one side of the elastic component far away from the rigid component, there is at least one pressing part designed to seal at least a portion of the user's nose; the annular comfort layer has a second accommodation area that communicates with the first accommodation area, covering at least part of the pressing part and jointly forming a sealed surface with the elastic component.

18 Claims, 15 Drawing Sheets

RESPIRATORY MASK WITH GOOD SEALING AND COMFORT

TECHNICAL FIELD

This disclosure relates to respiratory masks, and more specifically, to a respiratory mask with an annular comfort layer. The mask is configured to accommodate a portion of the user's face to prevent the leakage of pressurized gas supplied to the user.

BACKGROUND

Obstructive Sleep Apnea (OSA) is a common sleep-respiratory disorder affecting approximately 4% of men and 2% of women globally. It is characterized by repeated partial or complete cessation of respiration during sleep, each lasting more than 10 seconds. Such events can occur dozens or even hundreds of times in a single night. This cessation is due to the repetitive collapse of the patient's upper airway during sleep. Each collapse leads to a drop in blood oxygen saturation and can trigger a series of physiological and psychological responses, including awakening, tachycardia, cardiovascular diseases, daytime sleepiness, and mental fatigue. If not treated promptly, it can severely impact the patient's health and quality of life.

One of the common methods for treating OSA is Continuous Positive Airway Pressure (CPAP). CPAP devices deliver continuous positive air pressure to the patient's upper airway through a mask, maintaining airway patency and preventing upper airway collapse during sleep. CPAP treatment has been proven to significantly improve blood oxygen saturation, reduce daytime sleepiness, and enhance cognitive function. However, despite the widely accepted effectiveness of CPAP, its usage compliance is far from ideal. Studies have shown that about 50% of patients discontinue using it within 6 months after starting treatment. The mask is a critical part of CPAP treatment, as it is the part that contacts the patient. Its comfort level directly affects the degree to which the patient accepts the treatment. However, traditional CPAP mask designs have several problems, including discomfort, poor sealing, and causing facial pressure sores, all of which affect patient acceptance and compliance.

For example, comfort is one of the main concerns for patients regarding the mask. Since the mask needs to fit tightly against the user's face for effective sealing, excessive pressure often makes patients uncomfortable. Especially after long periods of wearing, the mask may exert too much pressure on the user's nose bridge, cheeks, forehead, etc., leading to issues like redness, pain, and bruising.

Secondly, sealing is also an important consideration in mask design. A good mask design should be able to provide comfort while maintaining good sealing to prevent gas leakage. However, the shape and size of faces vary from person to person, making it difficult for the mask to achieve ideal sealing. In many cases, the mask cannot fully conform to the face, leading to air leakage and affecting the effectiveness of the treatment.

To increase sealing, users can only resort to tightening the straps to exert pressure on the mask to achieve a sealed effect. However, the mask's sealing surface is not flat, and tightening the straps brings varying degrees of pressure to different areas of the face. When the mask is adequately sealed, users may find it intolerable to wear for extended periods. Moreover, the material of the traditional mask's sealing surface is not breathable. Prolonged wear of a tight mask may cause skin irritation or redness.

Additionally, if oils or sweat appear on the user's face during sleep, this can further degrade the mask's sealing performance. These issues not only make the patient uncomfortable but may even lead to discontinuation of use. Also, constantly adjusting the mask to alleviate discomfort may reduce its sealing, thereby affecting the treatment's effectiveness.

To address these issues, many improved mask designs have been proposed. For example, the market has started to sell mask liners, and masks made from softer materials are being used. However, although these designs have improved the comfort and sealing of masks to some extent, they still have some shortcomings. For example, using liners can reduce pressure sores caused by the mask being in tight contact with the skin. However, during sleep, there is some movement of the head, facial bones, and muscles, so the liner may shift or fall off during treatment, resulting in poor sealing. Using softer materials may compromise the structural stability of the mask, affecting its sealing capability.

SUMMARY

Given the aforementioned shortcomings, there is a need to develop a mask with excellent comfort and sealing properties. The present disclosure proposes a mask design that incorporates a foam pad. This design aims to improve the comfort and sealing of the mask, enhance compliance with CPAP treatment, and improve patients' quality of life. The mask incorporates a comfort layer made of absorbent material to enhance user comfort while ensuring proper sealing.

In an embodiment, the present disclosure provides a respiratory mask with good sealing and comfort, configured to enclose a user's nose and mouth by forming a sealing area between a lower lip area and a nasal bridge area, or to enclose only the user's nose by forming a sealing area between an upper lip area and the nasal bridge area, wherein the respiratory mask is configured to supply pressurized respiratory gas to the user's airway. The respiratory mask includes a rigid component having a farthest side away from the user's face having at least one gas delivery interface, with a nearest side of the rigid component closest to the user's face featuring an annular interface and forming a joint part along an outer edge of the annular interface; an elastic component containing a first accommodation area, which is designed for housing the user's mouth and the user's nose or only the nose and communicating with an inner cavity of the rigid component, with a side of the elastic component closest to the rigid component fixedly connected to the joint part, in which on a side of the elastic component facing away from the rigid component, there is a pressing part that seals at least a portion of the user's nose; and an annular comfort layer configured to seal at least part of the user's face when in use, containing a second accommodation area for housing the user's mouth and nose or only the nose, which is connected to the first accommodation area, in which the annular comfort layer is fixedly connected to the side of the elastic component facing away from the rigid component and covers at least part of the pressing part, forming a sealed surface that contacts the user's face together with the elastic component; the annular comfort layer is made of foam material.

In an embodiment, the rigid component is made of plastic material, the elastic component is made of silicone, rubber, thermoplastic elastomer, or silicone resin material, and the annular comfort layer is made of polyurethane, low-density polyether, or ethylene-vinyl acetate material.

In an embodiment, a cross-sectional shape of the annular comfort layer can be triangular, quadrilateral, pentagonal, or hexagonal.

In an embodiment, a perimeter of an inner edge of the annular comfort layer is greater than or equal to a perimeter of an inner edge on a side of the elastic component adjacent to the pressing part.

In an embodiment, a respiratory mask with good sealing and comfort is provided, which is configured to enclose a user's nose and mouth by forming a sealing area between a lower lip area and a nasal bridge area, or to enclose only the user's nose by forming a sealing area between an upper lip area and the nasal bridge area, wherein the respiratory mask is intended to supply pressurized respiratory gas to the user's airway. The respiratory mask includes a rigid component having a farthest side away from the user's face having at least one gas delivery interface, with a nearest side of the rigid component closest to the user's face featuring an annular interface and forming a joint part along an outer edge of the annular interface; an elastic component containing a first accommodation area, which is designed for housing the user's mouth and nose or only the nose and communicating with an inner cavity of the rigid component, with a side of the elastic component closest to the rigid component fixedly connected to the joint part, whereas on a side of the elastic component facing away from the rigid component, there is a pressing part that seals at least a portion of the user's nose; and an annular comfort layer configured to seal at least part of the user's face when in use, containing a second accommodation area for housing the user's mouth and nose or only the nose, which is connected to the first accommodation area, in which the annular comfort layer is fixedly connected to the side of the elastic component facing away from the rigid component and covers at least part of the pressing part, forming a sealed surface that contacts the user's face together with the elastic component, and the annular comfort layer is made of foam material. The annular comfort layer includes a first surface in contact with the user's face and a second surface connected to the elastic component, the angle α between the first surface and the second surface being at or between 0 to 80 degrees.

In one embodiment, the elastic component is made of silicone material, the annular comfort layer is made of polyurethane, low-density polyether, or ethylene-vinyl acetate material, and a perimeter of an inner edge of the annular comfort layer is greater than or equal to a perimeter of an inner edge on a side of the elastic component adjacent to the pressing part, and a shape of the second surface of the annular comfort layer is adapted to a shape on the side adjacent to the pressing part of the elastic component. In one embodiment, a height of the annular comfort layer is at or between 1 to 30 mm.

In one embodiment, the elastic component and the annular comfort layer are connected through molding, hot pressing, welding, foaming, or adhesive.

In an embodiment, another respiratory mask with good sealing and comfort is provided that is configured to enclose a user's nose and mouth by forming a sealing area between a lower lip area and a nasal bridge area, or to enclose only the user's nose by forming a sealing area between an upper lip area and the nasal bridge area, in which the respiratory mask is configured to supply pressurized respiratory gas to the user's airway. The respiratory mask includes a rigid component with a farthest side from the user's face having at least one gas delivery interface, with a side of the rigid component closest to the user's face featuring an annular interface and forming a joint part along an outer edge of the annular interface; an elastic component containing a first accommodation area, which is designed for housing the user's mouth and nose or only the nose and communicating with an inner cavity of the rigid component, with a side of the elastic component closest to the rigid component fixedly connected to the joint part, whereas on a side of the elastic component facing away from the rigid component, there is a pressing part that seals at least a portion of the user's nose; and an annular comfort layer configured to seal at least part of the user's face when in use, containing a second accommodation area for housing the user's mouth and nose or only the nose, which is connected to the first accommodation area, wherein the annular comfort layer is fixedly connected to the side of the elastic component facing away from the rigid component and covers at least part of the pressing part, forming a sealed surface that contacts the user's face together with the elastic component, and the annular comfort layer is made of absorbent material. The annular comfort layer also includes a first surface in contact with the user's face and a second surface connected to the elastic component.

In one embodiment, the elastic component is made of silicone material, and the annular comfort layer is made of textile material, which is nylon, spandex, or polyester; a perimeter of an inner edge of the annular comfort layer is greater than or equal to a perimeter of an inner edge on a side of the elastic component adjacent to the pressing part.

In one embodiment, a height of the annular comfort layer is uniform.

In one embodiment, an angle α between the first surface and the second surface of the annular comfort layer is at or between 0 to 80°.

In yet another embodiment, a respiratory mask with good sealing and comfort is provided, which is configured to enclose a user's nose and mouth by forming a sealing area between a lower lip area and a nasal bridge area, or to enclose only the user's nose by forming a sealing area between an upper lip area and the nasal bridge area, in which the respiratory mask is intended to supply pressurized respiratory gas to the user's airway. The respiratory mask includes a rigid component with a farthest side from the user's face having at least one gas delivery interface, with a side of the rigid component closest to the user's face featuring an annular interface and forming a joint part along an outer edge of the annular interface; an elastic component, configured to adjust the distance between the rigid component and the user's face, containing a first accommodation area, which is designed for housing the user's mouth and nose or just the nose and communicating with an inner cavity of the rigid component, with a side of the elastic component closest to the rigid component fixedly connected to the joint part, and a side of the elastic component facing away from the rigid component having a non-thin area and at least one thin area, with a wall thickness of the thin area at or between 0.2 to 2 mm; and an annular comfort layer configured to seal at least part of the user's face when in use, containing a second accommodation area for housing the user's mouth and nose or only the nose, which is connected to the first accommodation area. The annular comfort layer is fixedly connected to the side of the elastic component facing away from the rigid component and covers at least part of the elastic component, with the annular comfort layer made of at least one absorbent material. The annular comfort layer also includes a first surface that contacts the user's face and a second surface that connects to the elastic component, in which the distance variation between the first surface of the annular comfort layer and the rigid component will yield at least two different values when applying the same force in a constant direction to different positions of the annular comfort layer.

In one embodiment, both the thin area and the non-thin area are at least partially in contact with the user's face, and the thickness of at least one portion of the thin area that contacts the user's face is 7%-60% of a thickness of a portion of the non-thin area that contacts the user's face.

In one embodiment, the thin area corresponds to at least one of the user's nose or mouth areas.

In one embodiment, the elastic component is made of non-breathable material, and the annular comfort layer is made of foam material, textile material, or a composite material of foam and textile, the foam material being polyurethane.

In another embodiment, a respiratory mask with good sealing and comfort is provided, configured to enclose a user's nose and mouth by forming a sealing area between a lower lip area and a nasal bridge area, or to enclose only the user's nose by forming a sealing area between an upper lip area and the bridge, in which the respiratory mask is intended to supply pressurized respiratory gas to the user's airway. The respiratory mask includes a rigid component having a farthest side away from the user's face having at least one gas delivery interface, and a nearest side of the rigid component closest to the user's face featuring an annular interface and forming a joint part along an outer edge of the annular interface; an elastic component, configured to adjust the distance between the rigid component and the user's face, containing a first accommodation area, which is designed for housing the user's mouth and nose or just the nose and communicating with an inner cavity of the rigid component, with a side of the elastic component closest to the rigid component fixedly connected to the joint part, and a side of the elastic component facing away from the rigid component having a non-thin area and at least one thin area, with a wall thickness of the thin area at or between 0.2 to 2 mm; and an annular comfort layer configured to seal at least part of the user's face when in use, containing a second accommodation area for housing the user's mouth and nose or just the nose, which is connected to the first accommodation area, wherein the annular comfort layer is fixedly connected to the side of the elastic component facing away from the rigid component and covers at least part of the elastic component, forming a sealed surface that contacts the user's face together with the elastic component, wherein the annular comfort layer is made of at least one absorbent material, and includes a first surface that contacts the user's face and a second surface that connects to the elastic component.

In one embodiment, an angle α between the first surface and the second surface is at or between 0 to 80°, and the thin area corresponds to at least one of the user's nose or mouth areas.

In one embodiment, the elastic component is made of silicone, rubber, thermoplastic elastomer, or silicone resin material, and the absorbent material is foam material, textile material, or a composite of foam and textile materials.

In one embodiment, the elastic component and the annular comfort layer are connected in a non-removable manner.

Implementing this disclosure of a respiratory mask with good sealing and comfort can achieve at least the following beneficial effects:

Firstly, the disclosure replaces existing technology by setting up the surface of the respiratory mask that contacts the user as a combination of an annular comfort layer and an elastic component. In this design, the first surface of the annular comfort layer seals at least part of the user's face, while the second surface covers at least part of the elastic component. By changing the material covering the face, the comfort and sealing performance of the respiratory mask are improved. This design has several advantages:

The combination of the elastic component and the annular comfort layer allows the respiratory mask to conform to different areas of the face with varying degrees of deformation, fitting the facial contours more closely and achieving better sealing. Furthermore, the joint contact of the elastic component and the annular comfort layer can take the uneven pressure brought by the tightening headband across the face, reducing the likelihood of red marks or pressure sores, and thus increasing comfort.

Additionally, during sleep, movements of the user's head coupled with facial sweating and oil secretion can shift the mask. The annular comfort layer has good breathability and can absorb sweat and oils from the face, keeping the user's face dry and reducing the possibility of mask displacement or diminished sealing performance, thereby ensuring the mask's sealing performance.

It's worth mentioning that there are also other products on the market that use foam (annular comfort layer) in masks to achieve high comfort and good sealing. However, to conform to the face, the foam in the nose area of such products is often made thinner than other areas and has larger hanging parts, making it prone to tearing and damage, preventing proper sealing. In contrast, the respiratory mask provided by this disclosure combines the elastic component and the annular comfort layer for sealing. By varying the wall thickness of the elastic component in the nose area, it conforms to the bridge of the nose for sealing, while the relatively flat parts of the face are sealed by the annular comfort layer. The use of elastic material for sealing in the easily damaged nose area makes it more durable and longer-lasting, while the use of the annular comfort layer for sealing in areas like the cheeks and chin, which are relatively flat and have fewer fluctuations, minimizes the risk of tearing. This ensures both maximum sealing performance and comfort, while also extending the lifespan of the respiratory mask.

Additionally, the respiratory mask of this disclosure is more environmentally friendly compared to existing technology that uses foam material. Traditional masks achieve sealing and therapeutic effects by adhering foam material shaped to fit the face to a flat silicone surface. In this scenario, a separate flat elastic component needs to be produced to match the foam material.

In contrast, the respiratory mask of this disclosure can achieve effective sealing on the face even when using a single elastic component. That is, the same elastic component can ensure both sealing and therapeutic effects in two different forms (with and without the annular comfort layer). Therefore, this disclosure innovatively adopts a modular design for the mask. The same elastic component offers two different usage effects. Compared to the existing technology, which requires a separately produced elastic component, this not only saves energy and raw materials but is also more environmentally friendly.

BRIEF DESCRIPTION OF THE DRAWINGS

To clarify the embodiments or existing technologies more clearly, the drawings used in the description of the embodiments or existing technologies will be briefly introduced below. Obviously, the drawings described below are just examples of embodiments of the disclosure. For those skilled in the art, other drawings can also be obtained based on the provided drawings without creative effort.

Figure 1:
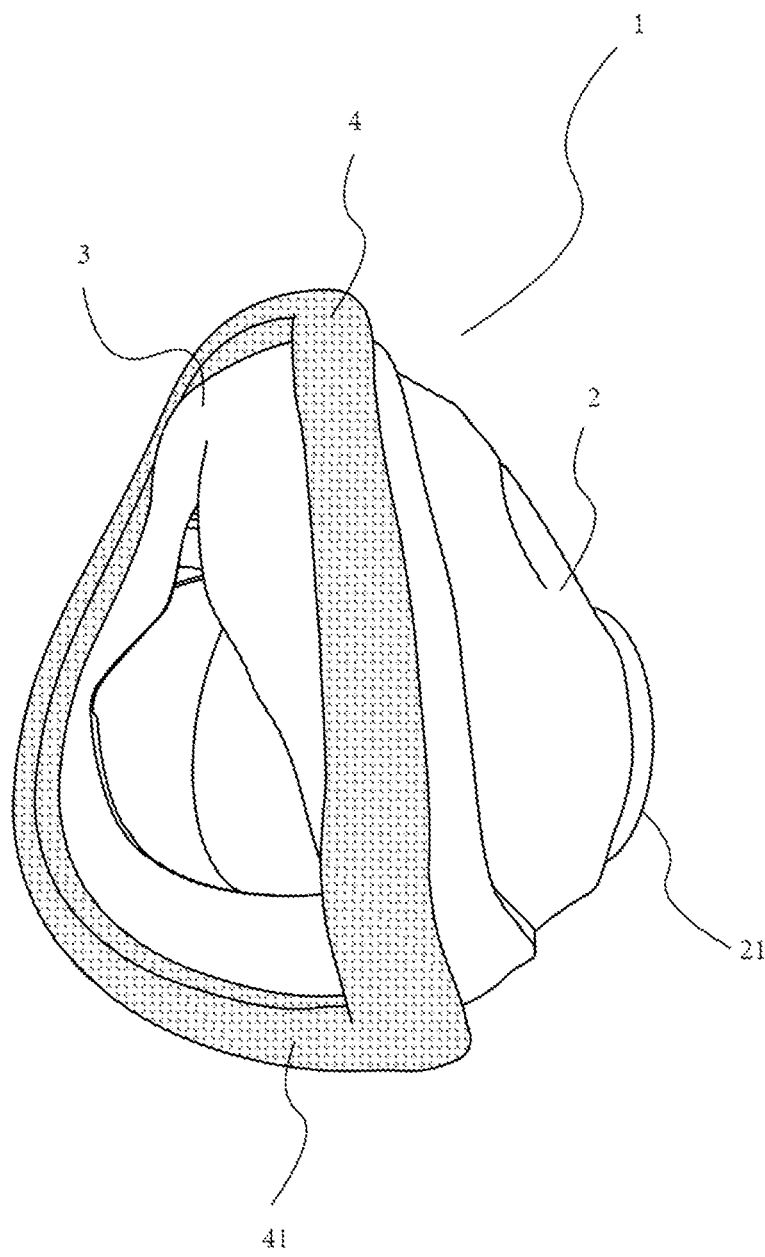
FIG. 1 is a three-dimensional assembly of a schematic view of a respiratory mask according to an embodiment.
Figure 2:
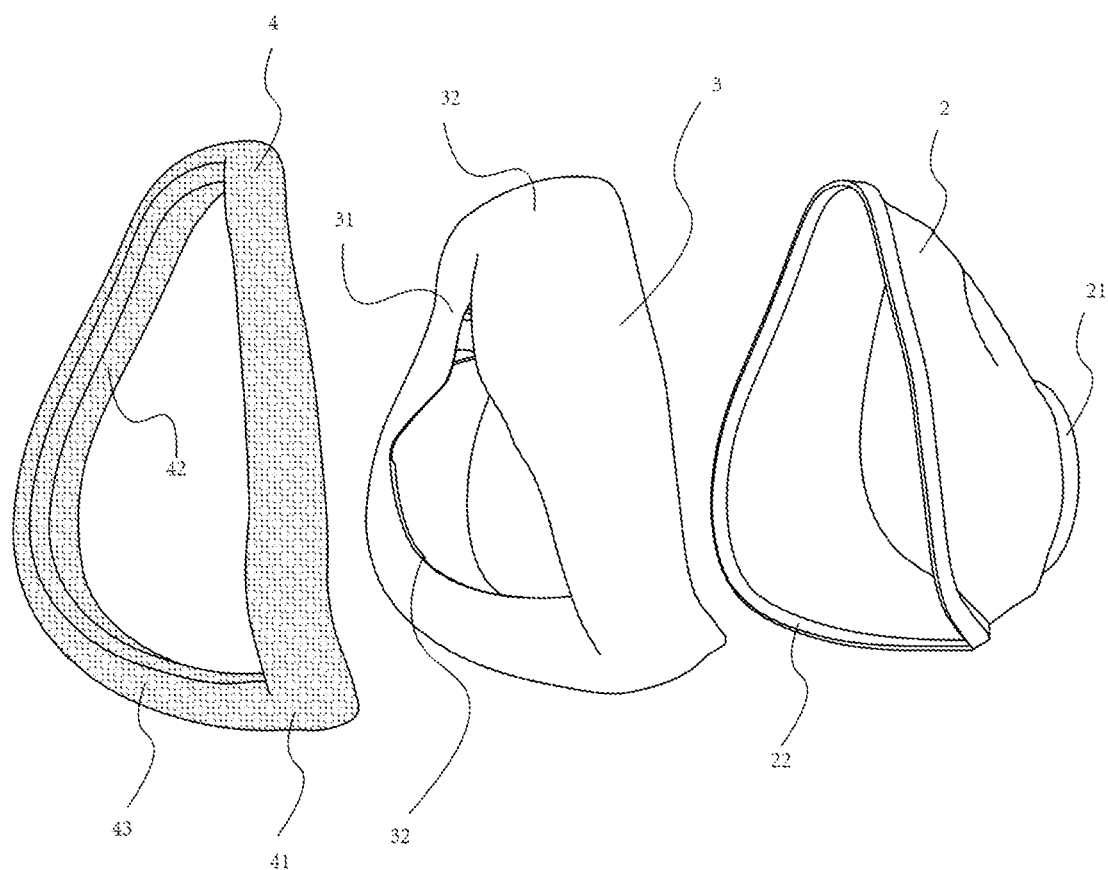
FIG. 2 is an exploded three-dimensional schematic view of the respiratory mask according to an embodiment.

The unified numbering explanation is as follows:
Respiratory mask 1;
Rigid Component 2;
Gas Delivery Interface 21;
Joint Part 22;
Elastic Component 3;
Nose Area 31;
Inner Edge of Elastic Component 32;
Thin Area 33;
Non-thin Area 34
Annular Comfort Layer 4;
First Surface 41;
Second Surface 42;
Mouth Area 43;
Inner Edge of Annular Comfort Layer 44

DETAILED DESCRIPTION

To make the objectives, features, and advantages of this disclosure more apparent and understandable, the following provides a detailed explanation of specific embodiments of this disclosure, along with accompanying illustrations. Many specific details are elaborated below to facilitate a full understanding of this disclosure. However, this disclosure can be embodied in many other ways different from those described here. Skilled persons in this field can make similar improvements without deviating from the essence of this disclosure, so this disclosure is not limited to the specific examples disclosed below.

This disclosure aims to solve the problems of traditional respiratory masks, where the elastic parts that contact the user's face are made of non-breathable materials like silicone. For example, when tightening the head strap to ensure a seal, these elastic parts can create excessive local pressure on the user's face, leading to red marks and pressure sores. Existing masks with foam material also have issues of being easily damaged and having pads that slip off. This disclosure provides a respiratory mask with an annular comfort layer. The sealing surface that contacts the user's face is composed of two components: an elastic component and an annular comfort layer, ensuring that the sealing surface, at least at the part where it contacts the user's nasal bridge, is made of elastic material to prevent air leakage around the nasal bridge. It also contacts the remaining areas through an annular comfort layer, distributing the force exerted on the user's face when tightening the head strap. This results in a uniform pressure on the user's face, thereby improving the user experience of wearing the respiratory mask.

The following explains a few structural designs of this respiratory mask with good sealing and comfort, based on specific embodiments.

Embodiment 1

The respiratory mask, according to an embodiment, has good sealing and comfort, and is designed to either enclose the user's nose and mouth and form a sealing area between the lower lip area and the nasal bridge area, or to enclose just (or only) the user's nose and form a sealing area between the upper lip area and the nasal bridge area. In other words, the respiratory mask of this disclosure can either be designed in a smaller size to cover only the user's nose, providing pressurized breathing gas through the user's nostrils, or in a larger size to cover both the user's nose and mouth, supplying pressurized breathing gas through both the nostrils and the mouth, thereby meeting the needs of users with different usage habits and physiological conditions.

FIGS. 1 to 4 and 9 illustrate an embodiment of a respiratory mask 1 that includes a rigid component 2, an elastic component 3, and an annular comfort layer 4. The mask includes areas corresponding to the user's nose and mouth. The rigid component 2 can be made from any rigid material that ensures the strength and support of the component. In this embodiment, the rigid component 2 is made of plastic materials (polycarbonate material, polyamide material, acrylonitrile butadiene styrene material). The color of the rigid component 2 can be transparent, translucent, or opaque. Preferably, the rigid component 2 is transparent so that the user's usage condition can be observed, or alternatively, it is translucent. The side of the rigid component 2 farthest away from the user's face has at least one gas delivery interface 21, for receiving pressurized gas generated by a Continuous Positive Airway Pressure (CPAP) device. The gas delivery interface 21 can also accommodate a framework or connector that links to the Continuous Positive Airway Pressure device. The side of the rigid component 2 closest or nearest to the user's face features an annular interface, and a joint part 22 is formed on the outer edge of the annular interface. The rigid component 2 connects to the elastic component 3, fixing the contour shape and providing some support for the elastic component 3.

On the elastic component 3, there is a first accommodation area for housing the user's mouth and nose or only the nose, which is connected to the inner cavity of the rigid component 2. The side of the elastic component 3 closest to the rigid component 2 is fixedly connected to the joint part 22. The connection between the elastic component 3 and the joint part 22 of the rigid component 2 can be injection molded, chemically bonded with adhesive later, or joined using clamps or buckles. On a side of the elastic component 3 facing away from the rigid component 2, there is a pressing part that seals at least a portion of the user's nose. The pressing part contacts at least a portion of the user's nose, such as the nasal bridge, the wings of the nose, or the side walls of the nose, or a combination of these. The same side of the elastic component 3 as that of the pressing part is used for connecting with the annular comfort layer 4.

The elastic component 3 is configured to adjust a distance between the rigid component 2 and the face. To ensure that the elastic component 3 has enough deformation space for fitting the face during use and to avoid the rigid component 2 directly applying pressure to the face when the user tightens the headband, the height between the edge of the elastic component 3 near the pressing part and the edge of the elastic component 3 near the joint part 22 is at least 8 mm. Different areas of the elastic component 3 can have different heights, and the height can range at or between 8 to 40 mm. In an embodiment, the elastic component 3 is made of non-breathable material and is made from soft, deformable materials, such as silicone, rubber, thermoplastic elastomers, or silicone resin. More specifically, the elastic component 3 is made of silicone material. Additionally, the side of the elastic component 3 facing away from the rigid component 2 has a non-thin area (i.e. the area excluding the thin area) and at least one thin area 33. The wall thickness of the thin area 33 is at or between 0.2 to 2 mm. The thin area 33 corresponds to at least one area of the user's nose area 31 or mouth area 43. The purpose of this design is to ensure that, under therapeutic pressure, the thin area 33 can tightly adhere to the user's face, forming a good seal. The connection between the thin area 33 and the non-thin area can either be smooth and continuous (with no visible changes to the naked eye) or abrupt (with a visible demarcation line). In this embodiment, both the thin area 33 and the non-thin area are in at least partial contact with the user's face. The thickness of at least part of the thin area in contact with the user's face is 7%-60% of the thickness of the part of the non-thin area in contact with the user's face. In another variation, the thin area 33 is in complete contact with the user's face, while the non-thin area is not directly in touch with the user's face.

Figure 3:
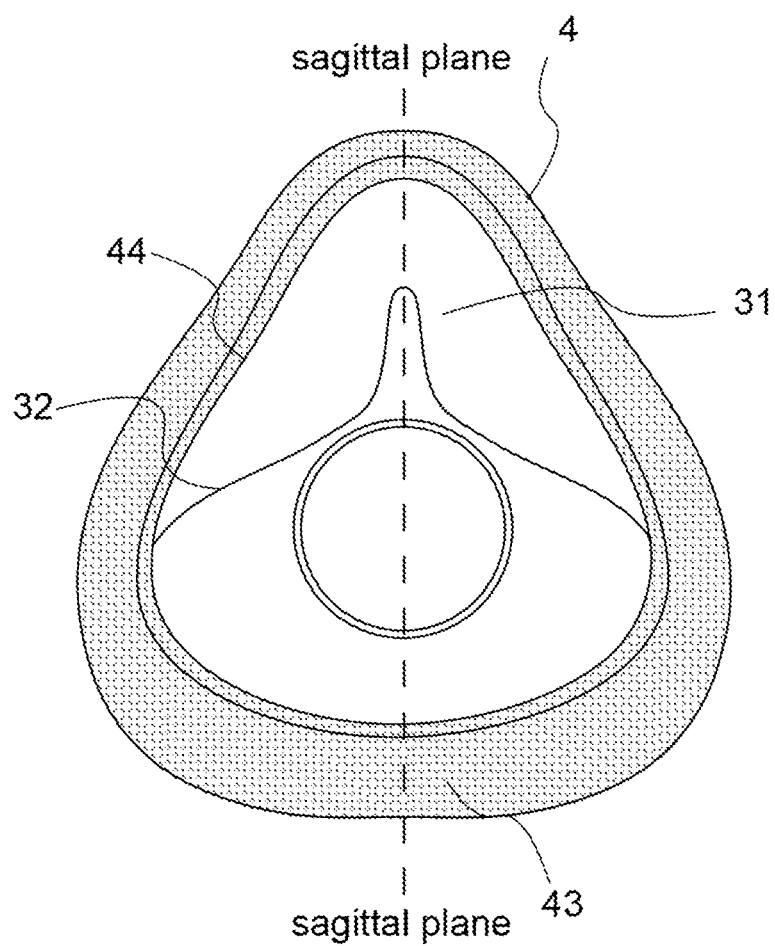
FIG. 3 is a schematic front view of a respiratory mask according to an embodiment.
Figure 4:
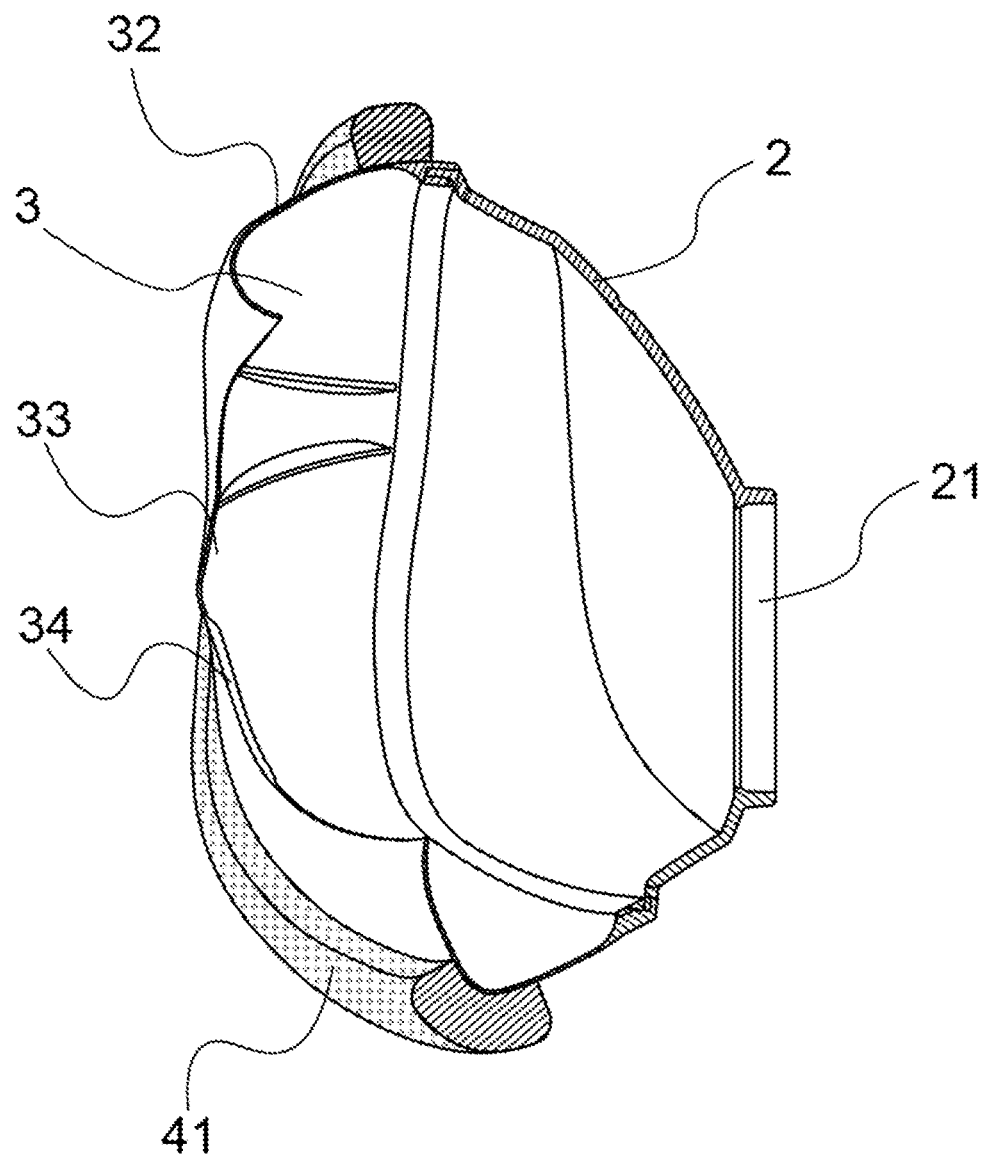
FIG. 4 is a cross-sectional view in the sagittal plane direction from FIG. 3.

The annular comfort layer 4 is configured to seal at least a portion of the user's face during use. The annular comfort layer 4 contains a second accommodation area that houses the user's mouth and nose or just the nose and is connected to the first accommodation area. The annular comfort layer 4 is fixedly connected to the side of the elastic component 3 facing away from the rigid component 2 and covers at least a part of the pressing section. Together, the annular comfort layer 4 and the elastic component 3 form a sealing surface in contact with the user's face (as shown in FIG. 3). The elastic component 3 and the annular comfort layer 4 are connected in a non-removable manner. In some embodiments, the connection between the annular comfort layer 4 and the elastic component 3 is detachable. In this embodiment, the elastic component 3 and the annular comfort layer 4 are connected through molding, hot pressing, welding, foaming, or adhesive. In some variations, the connection between the elastic component 3 and the annular comfort layer 4 can also be made indirectly through auxiliary materials (for example, polyurethane films, polymer films, acrylic films, and polyamide films) acting as an interlayer. In another variation, they can also be connected through auxiliary fittings like clips or bands. The material of the annular comfort layer 4 is composed of two or more composite materials, such as foam materials, textile materials, novel absorbent materials, or any other biocompatible materials. In some variations, the annular comfort layer 4 can also be a single material. There are various ways to form the composite, such as adhesive bonding (binding different materials together with glue) or flame bonding (melting materials by heating, and then bonding different materials due to their inherent adhesiveness). In this embodiment, the annular comfort layer 4 is made of foam material, specifically polyurethane, low-density polyether, or ethylene-vinyl acetate material. Furthermore, the annular comfort layer 4 has a three-dimensional shape, with a density at or between 10 to 200 kg/m$^3$. To avoid affecting the therapeutic effect, the permeability of the annular comfort layer 4 is less than 50 L/min.

It should be noted that the annular comfort layer 4 and the elastic component 3 together form a sealing surface in contact with the user's face to address the following issues in existing technologies. Traditional respiratory masks often use silicone or similar non-breathable materials to create a facial seal. With long-term wear and pressure, users often feel discomfort, and their faces may show red marks or develop pressure sores. Additionally, the non-breathable nature of these materials can lead to sweating and oil secretion on the user's face during use, causing the mask to shift or lose its sealing properties when the head moves during sleep.

Therefore, in various embodiments as discussed herein, the sealing surface is a combination of the annular comfort layer 4 and the elastic component 3. In the nose area, the elastic component 3 remains in contact with at least part of the user's nose, while the rest of the sealing surface is comprised of the annular comfort layer 4. The annular comfort layer 4 has better deformability than the elastic component 3, allowing it to distribute the uneven pressure exerted by the tightening straps across the face, thereby providing a more comfortable user experience. Moreover, the annular comfort layer 4 is breathable and can absorb sweat and oils from the face, keeping the user's skin dry and reducing the likelihood of mask displacement, ensuring a good seal. In contrast to existing masks that have foam-based sealing surfaces, where the foam is usually made thinner in the bridge of the nose for a better seal and comfort, which can result in more significant sagging. This leads to squeezing on the nose area during use, causing tearing or damage. Additionally, the considerable height difference between the nasal bridge and the facial area makes leakage very likely on the sides of the nose. In the embodiments discussed herein, the non-breathable elastic component 3 is still used in the nose area, eliminating the possibility of leakage; and in areas like the cheeks and chin that are relatively flat, the annular comfort layer 4 is applied, which has less tendency to tear due to its lesser variation in surface elevation. This design maximizes both sealing effectiveness and comfort during use.

Figure 5:
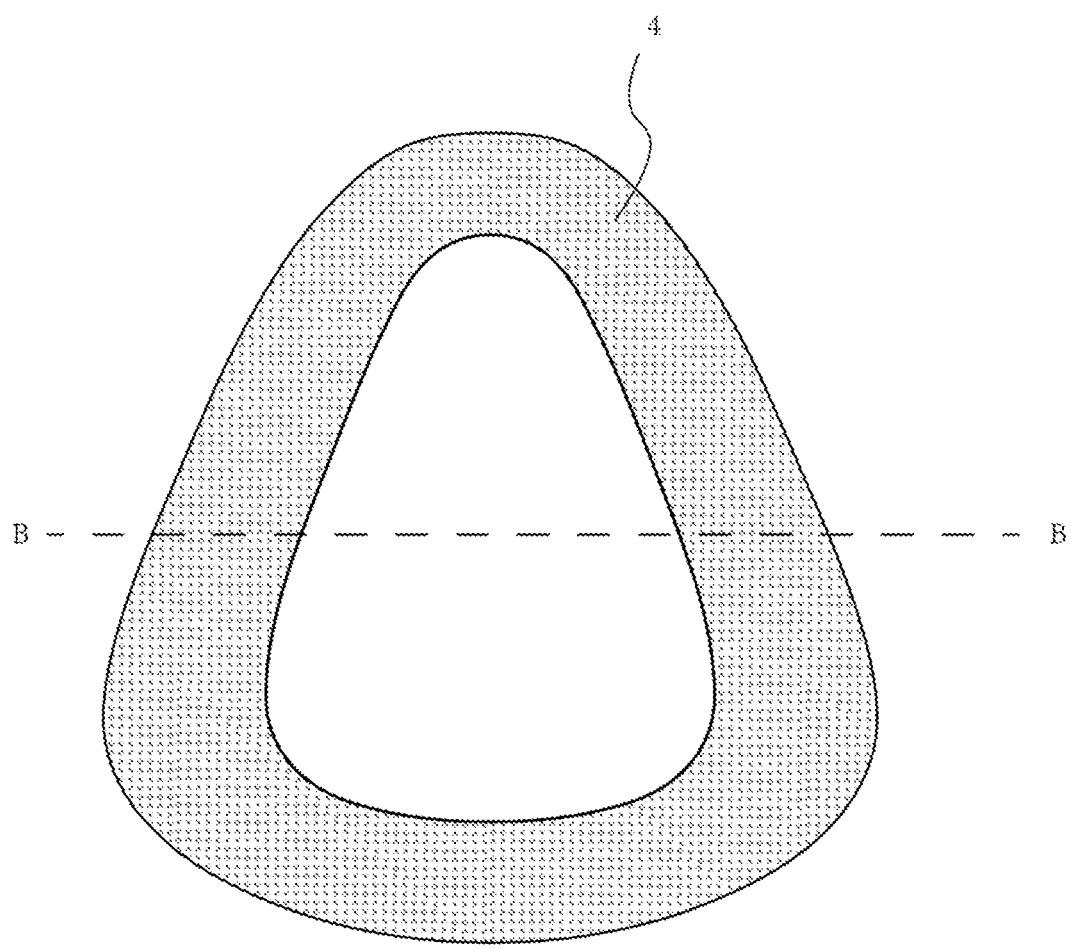
FIG. 5 is a schematic front view of an annular comfort layer according to an embodiment.
Figure 6:
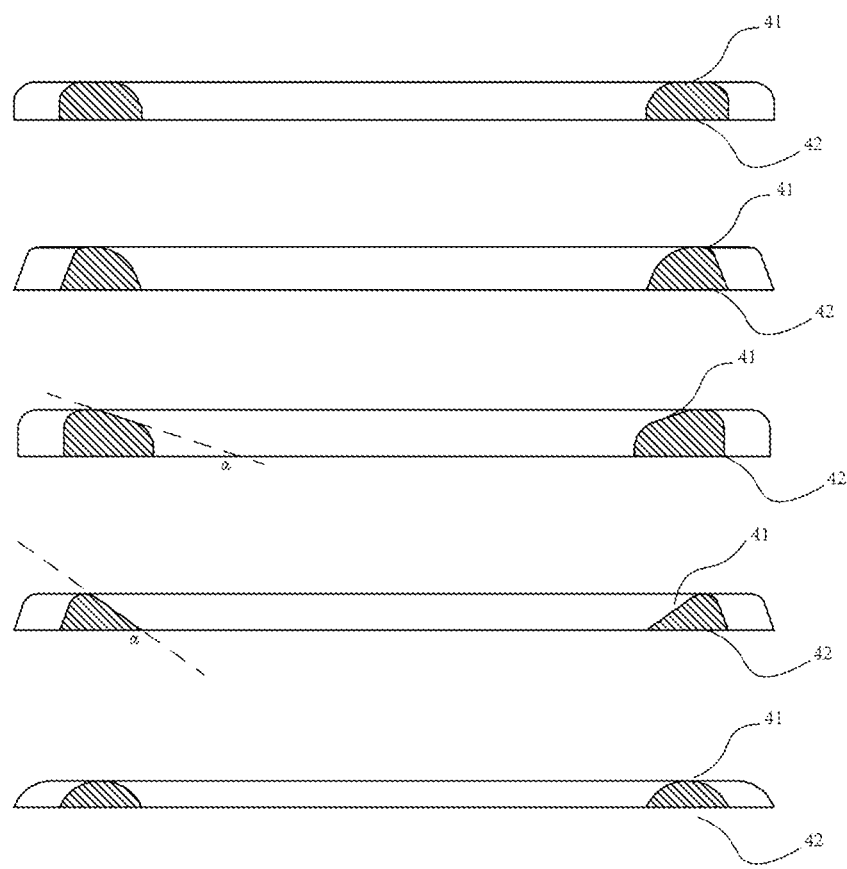
FIG. 6 is a cross-sectional view in the B-B direction according to multiple embodiments of FIG. 5.

Referring to FIGS. 1, 5, and 6, the annular comfort layer 4 features an annular contour (a shape that is continuous and joined end-to-end). The inner edge of the annular comfort layer 4 can encircle the user's nose or the nose and mouth. To achieve simultaneous sealing of the user's face by both the elastic component 3 and the annular comfort layer 4, the perimeter of the inner edge 44 of the annular comfort layer 4 is greater than or equal to the perimeter of the inner edge 32 on the side of the elastic component 3 adjacent to the pressing part. As shown in FIG. 6, the cross-sectional shape of the annular comfort layer 4 can be triangular, quadrilateral, pentagonal, or hexagonal. The annular comfort layer 4 includes a first surface 41 that contacts the user's face and a second surface 42 that connects to the elastic component 3. Typically, when in use, the first surface 41 generally conforms to the shape of the face. To improve comfort, the edges of the first surface 41 are usually rounded. The second surface 42 is generally flat and adapted to match the shape of the side of the elastic component 3 adjacent to the pressing part. For comfort, the first surface 41 should generally follow the contour of the face. The first surface 41 and the second surface 42 can be parallel or angled to better fit the facial contours. As FIG. 6 demonstrates, the angle α between the first surface 41 and the second surface 42 can be at or between 0 to 80°. To optimize the user experience, the height of the annular comfort layer 4 should be controlled to avoid creating a step difference when it comes into contact with the elastic component 3 when the annular comfort layer contacts the user's face. Additionally, the width of the annular comfort layer 4 should be sufficient to fully cover the face, excluding the nose area 31, when the respiratory mask 1 contacts the user's face. In this embodiment, the height of the annular comfort layer 4 can be at or between 1 to 30 mm, and the ratio of the width to the height is at or between 0.1 to 30.

Figure 7:
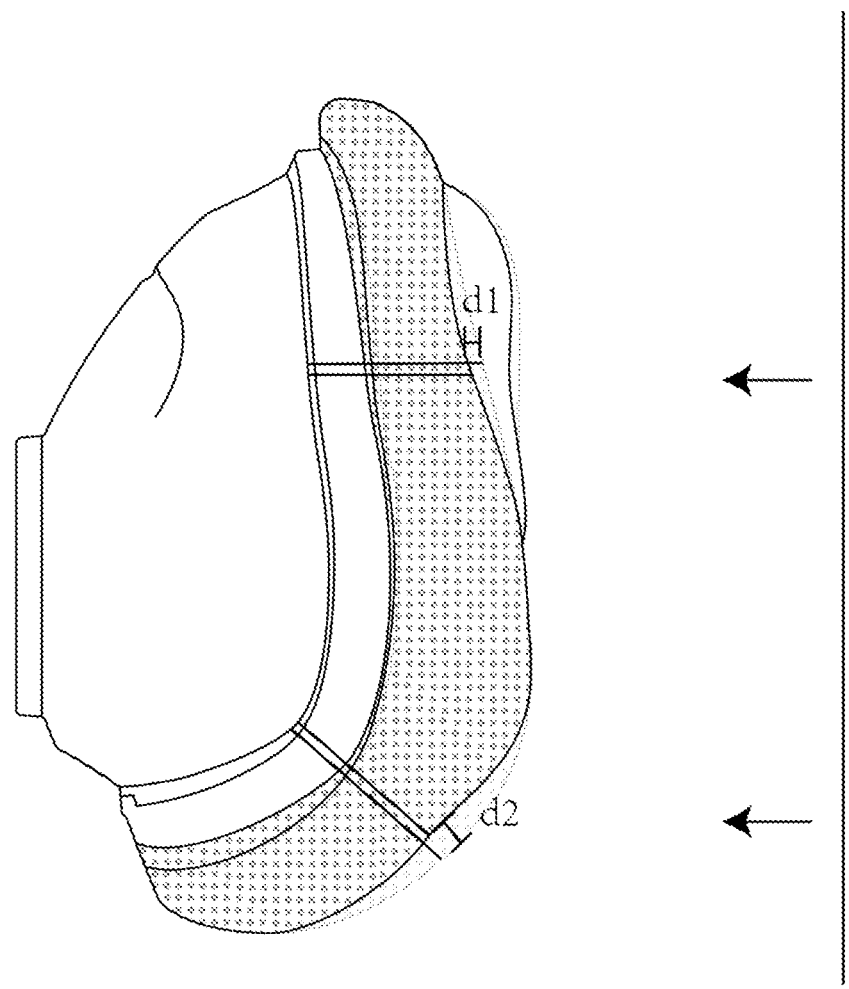
FIG. 7 is a schematic diagram of force exerted on an annular comfort layer according to an embodiment.
Figure 8:
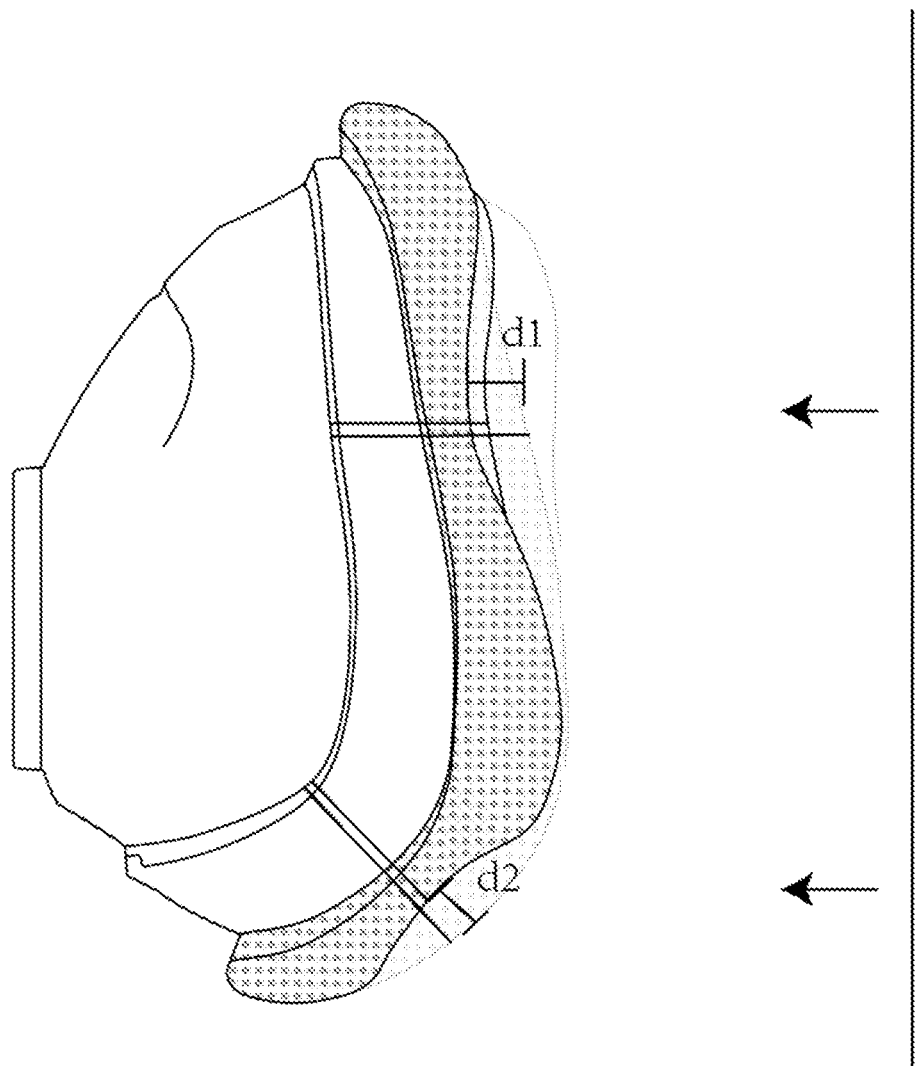
FIG. 8 is a schematic diagram of force exerted on an annular comfort layer according to another embodiment.
Figure 9:
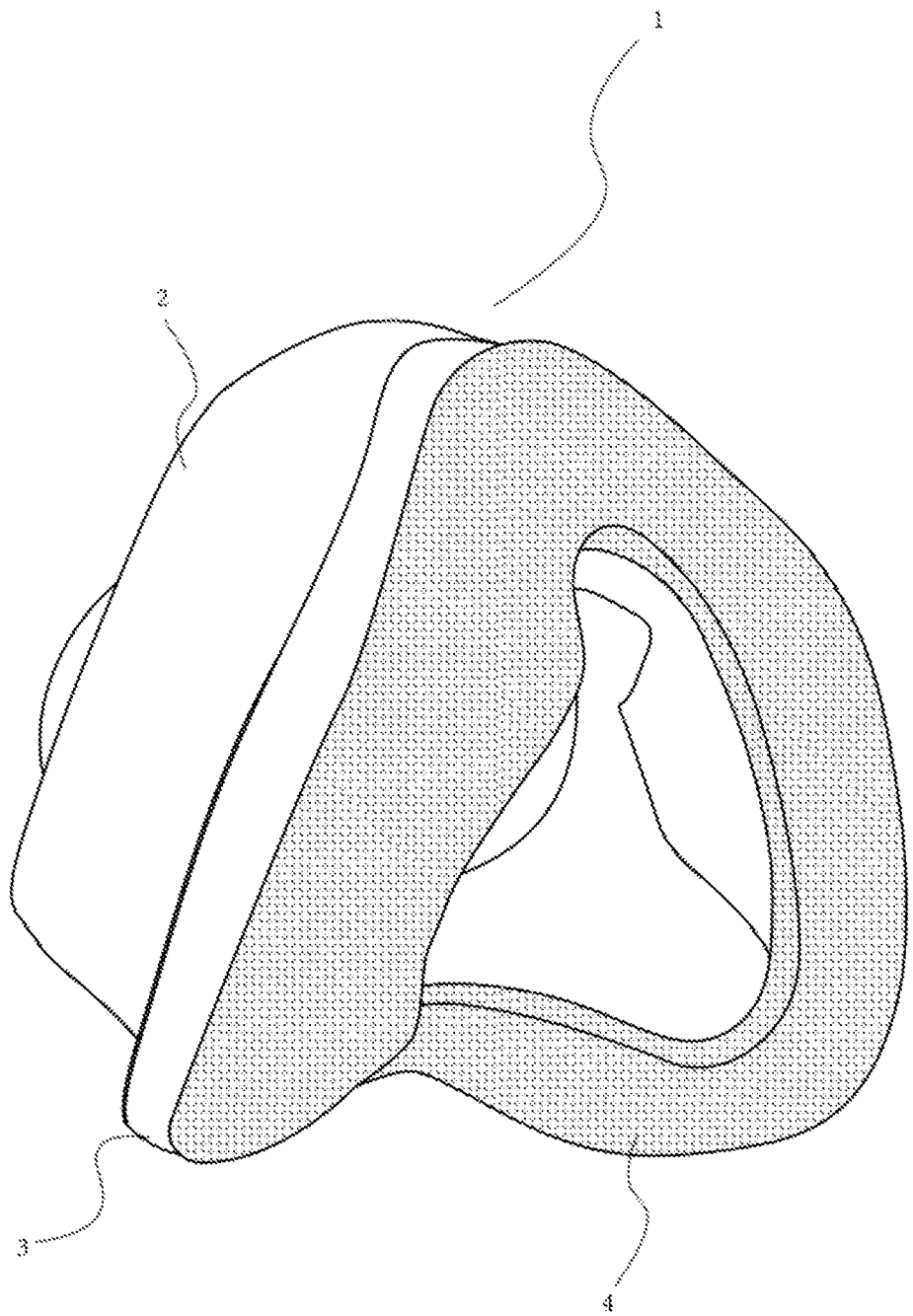
FIG. 9 is a three-dimensional schematic view of a nasal mask according to an embodiment.

Referring to FIGS. 7 and 8, to ensure that the respiratory mask 1 can automatically conform to the facial contours of most people during use, while maintaining sealing and comfort, different areas of the respiratory mask 1 need to deform to varying degrees to adapt to facial contours. Furthermore, the pressure exerted on different areas of the face should generally be uniform. In this disclosure, the face mask is designed by adjusting the wall thickness of the elastic component 3 or the shape and height of the annular comfort layer 4. When a constant force is applied in a fixed direction (perpendicular to the sagittal plane) to different positions of the comfort layer, the force-applied points of the elastic component 3 and annular comfort layer 4 will deform to varying extents. That is, when the same force is applied in a fixed direction to different positions of the annular comfort layer 4, the distance between the first surface 41 of the annular comfort layer 4 and the rigid component 2 will yield at least two different values. In this way, during the wearing process, the elastic component 3 and the annular comfort layer 4 can deform to varying degrees in accordance with facial contours. Additionally, the soft and elastic material can distribute the pressure across the face, achieving a more comfortable wearing experience. In this embodiment, the height of the annular comfort layer 4 is uniform. The changes in the annular comfort layer 4 when subjected to pressure are shown in FIG. 7. In the figure, d1 and d2 represent the deformation values of the first surface 41 at two different positions of the annular comfort layer 4 before and after the force is applied, i.e., the two different values of distance variation between the first surface 41 of the comfort layer 4 and the rigid component 2. In some variations, the height of the annular comfort layer 4 is not uniform; the changes in the annular comfort layer 4 under pressure in these cases are shown in FIG. 8.

Embodiment 2

Figure 10:
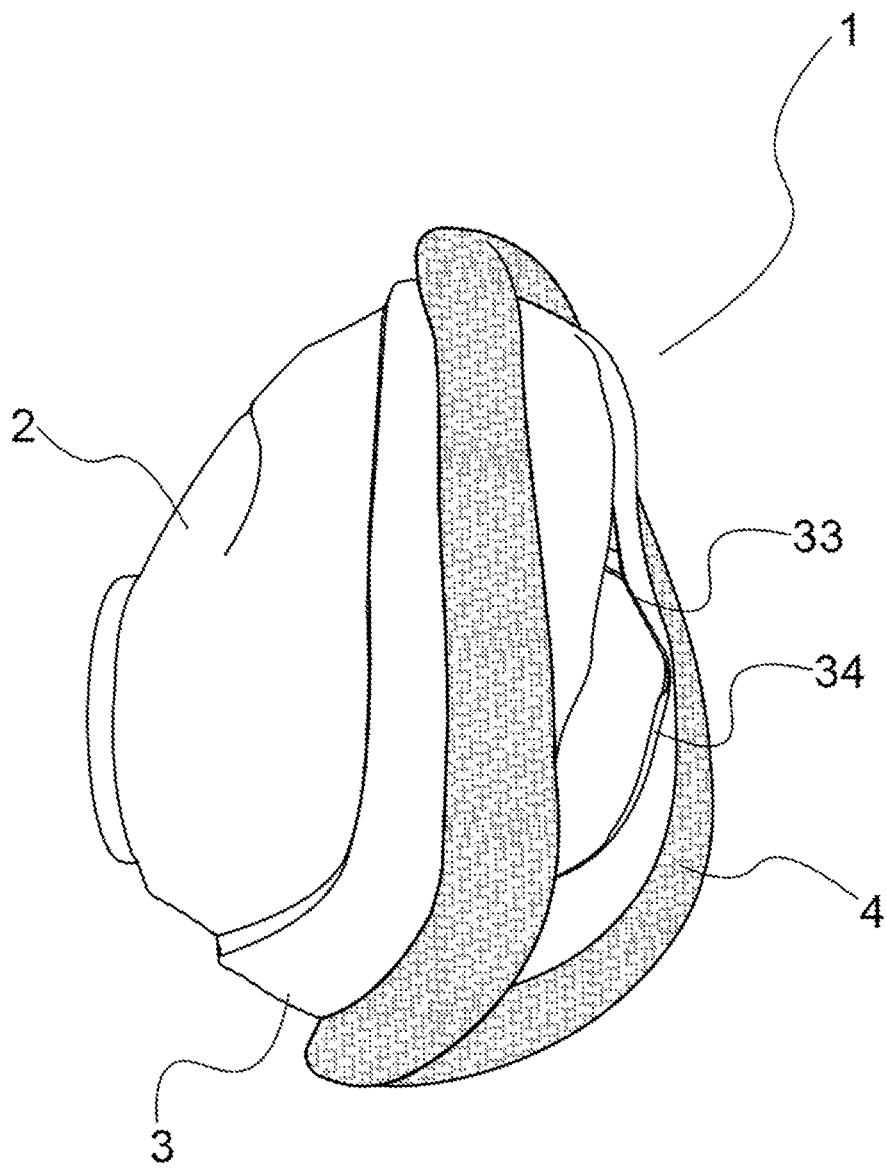
FIG. 10 is a three-dimensional schematic view of a respiratory mask according to an embodiment.
Figure 11:
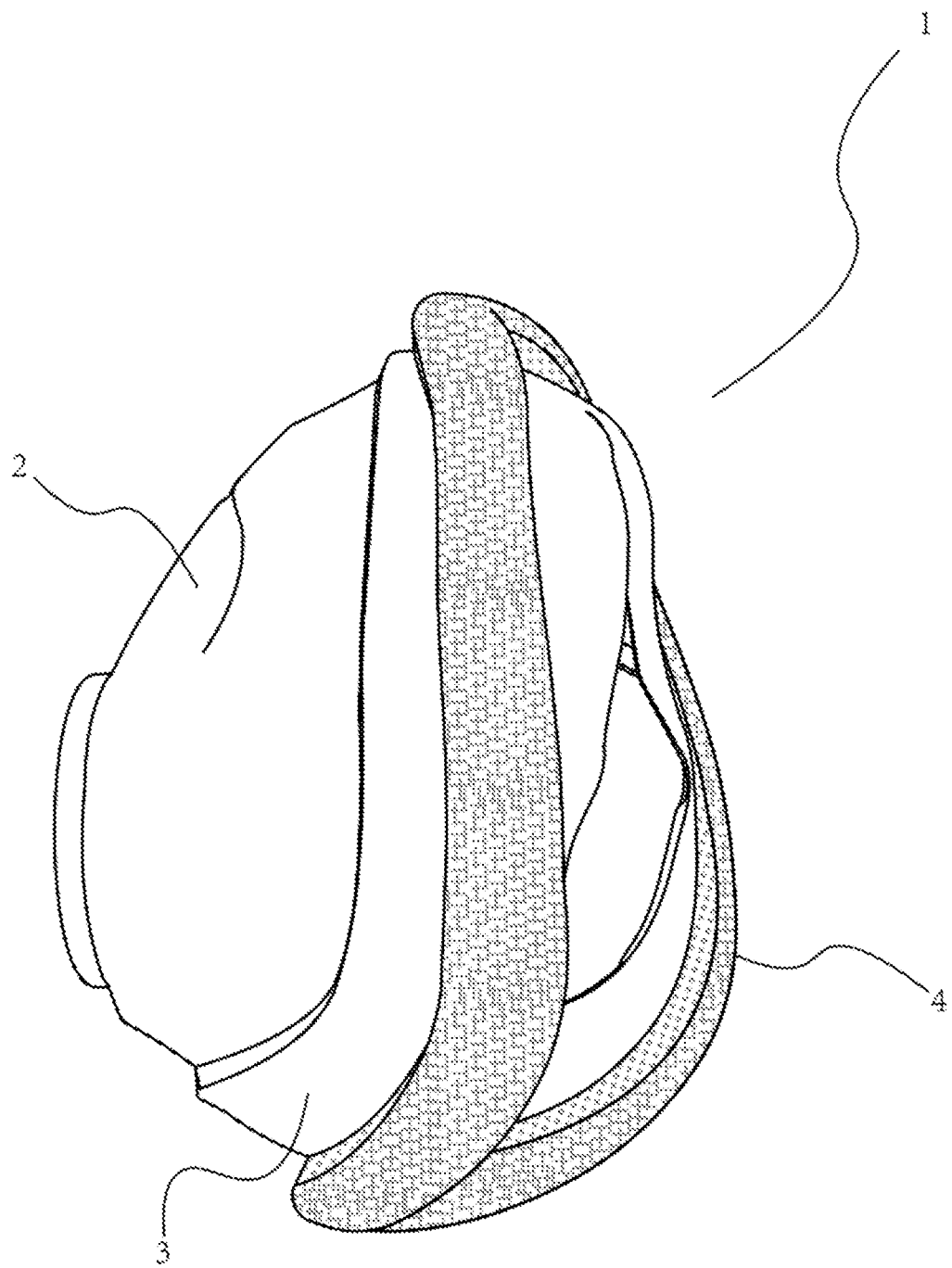
FIG. 11 is a three-dimensional schematic view of a respiratory mask according to an embodiment.
Figure 12:
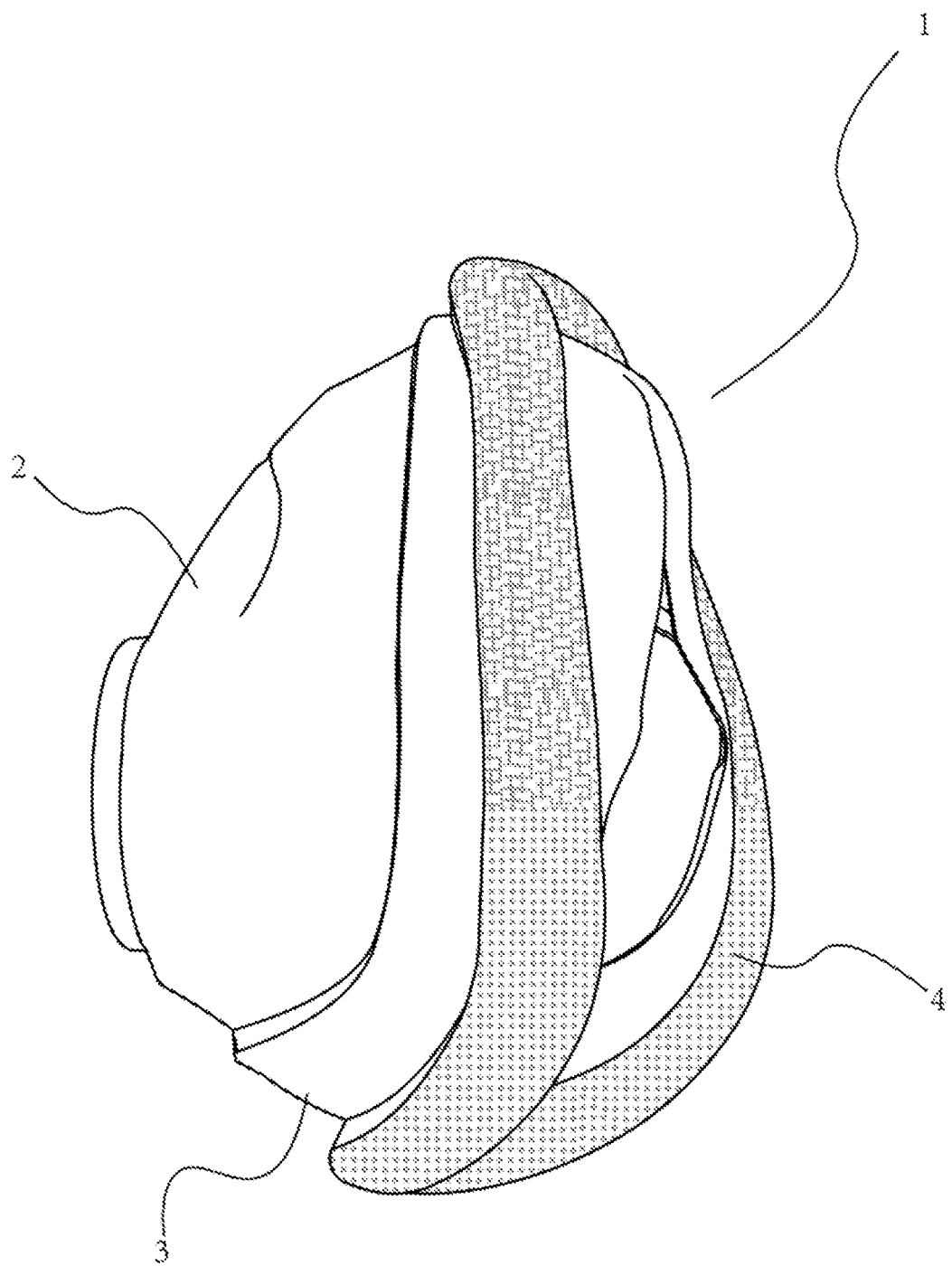
FIG. 12 is a three-dimensional schematic view of a respiratory mask according to an embodiment.

This embodiment includes a respiratory mask with good sealing and comfort, configured to enclose a user's nose and mouth, forming a sealing area between a lower lip and a nasal bridge, or to enclose only the user's nose by forming a sealing area between an upper lip area and the nasal bridge area, wherein the respiratory mask is intended to supply pressurized respiratory gas to the user's airway, which includes rigid component 2, elastic component 3, and annular comfort layer 4. The difference between the respiratory mask 1 provided in this embodiment and that in Embodiment 1 lies in the material of the annular comfort layer 4. As shown in FIGS. 10 to 12 (nasal mask not shown), the annular comfort layer 4 in this embodiment is made of at least one absorbent material. Specifically, the annular comfort layer 4 is made of foam material, textile material, or a composite of foam and textile materials. The foam material may include polyurethane, low-density polyether, ethylene-vinyl acetate, rubber foam, or latex foam. The foam component further enhances the elasticity of the respiratory mask 1, allowing it to better conform to the face. The textile material improves the water-absorbing capacity of the annular comfort layer 4 made solely from foam material. Compared to foam material, the surface of the textile material is smoother and softer, which benefits the user by improving sleep quality and therapeutic efficacy, thereby increasing treatment compliance.

This embodiment can have three variations: As shown in FIG. 10, the main body of the annular comfort layer 4 is made of foam material, which is fully wrapped in textile material. This means that the first surface 41 of the annular comfort layer 4, the one that comes into contact with the face, is made of textile material. The textile material fully encloses the foam, reducing the likelihood of tearing and thus extending the lifespan of the respiratory mask 1. As depicted in FIG. 11, the textile material only covers the surface of the foam that is adjacent to the user's face. This design not only prevents tearing of the foam but also retains its breathability. The part of the foam exposed to the air can evaporate absorbed moisture and heat more effectively, increasing the dryness and decreasing the drying time of the annular comfort cushion 4. As illustrated in FIG. 12 (the figure only shows the textile material covering the upper part of the foam material, but it could also cover other parts, like the lower part that contacts the mouth area; or for instance, it could cover the foam in the area of the cheekbones where the mask contacts more prominent facial bones), the textile material partially covers the foam. This allows both the foam and the textile materials to be in contact with the user's face simultaneously.

Embodiment 3

Figure 13:
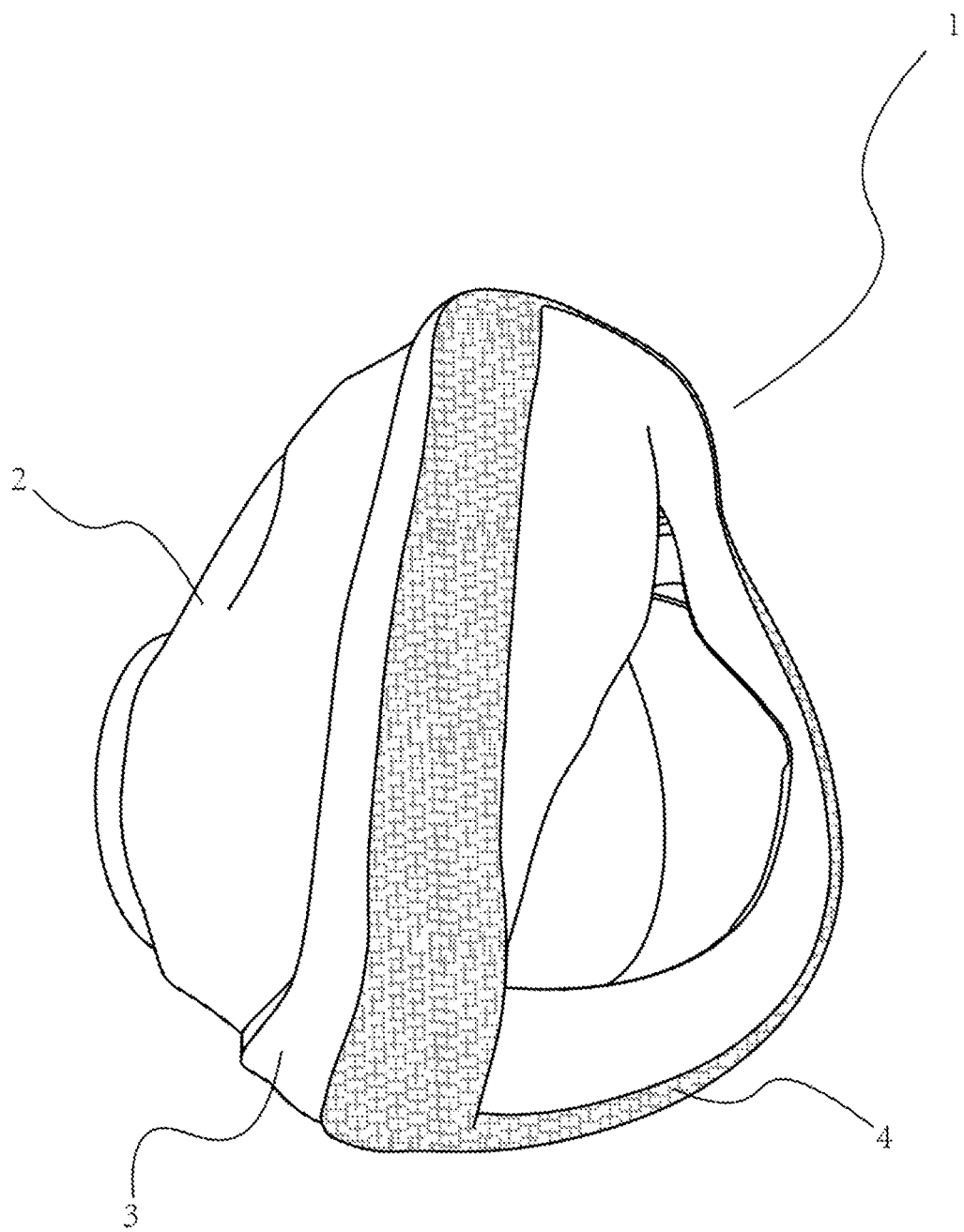
FIG. 13 is a three-dimensional schematic view of a respiratory mask according to an embodiment.

This embodiment includes a respiratory mask with good sealing and comfort, configured to enclose a user's nose and mouth by forming a sealing area between a lower lip and a nasal bridge, or to enclose only the user's nose by forming a sealing area between an upper lip area and the nasal bridge area, wherein the respiratory mask is intended to supply pressurized respiratory gas to the user's airway, which includes a rigid component 2, an elastic component 3, and an annular comfort layer 4. The difference between this respiratory mask 1 and the respiratory mask in Embodiment 1 lies in the material of the annular comfort layer 4. As depicted in FIG. 13 (which does not show the nasal mask), the annular comfort layer 4 in this embodiment is made of absorbent material, specifically textile material such as nylon, spandex, or polyester. To be more precise, the annular comfort layer employs a single layer of textile material that is both lightweight and breathable. This allows for a soft touch against the skin while maintaining the maximum contour of the side of the elastic component 3 adjacent to the pressing area. This design allows the mask to better conform to the user's facial features.

Embodiment 4

Figure 14:
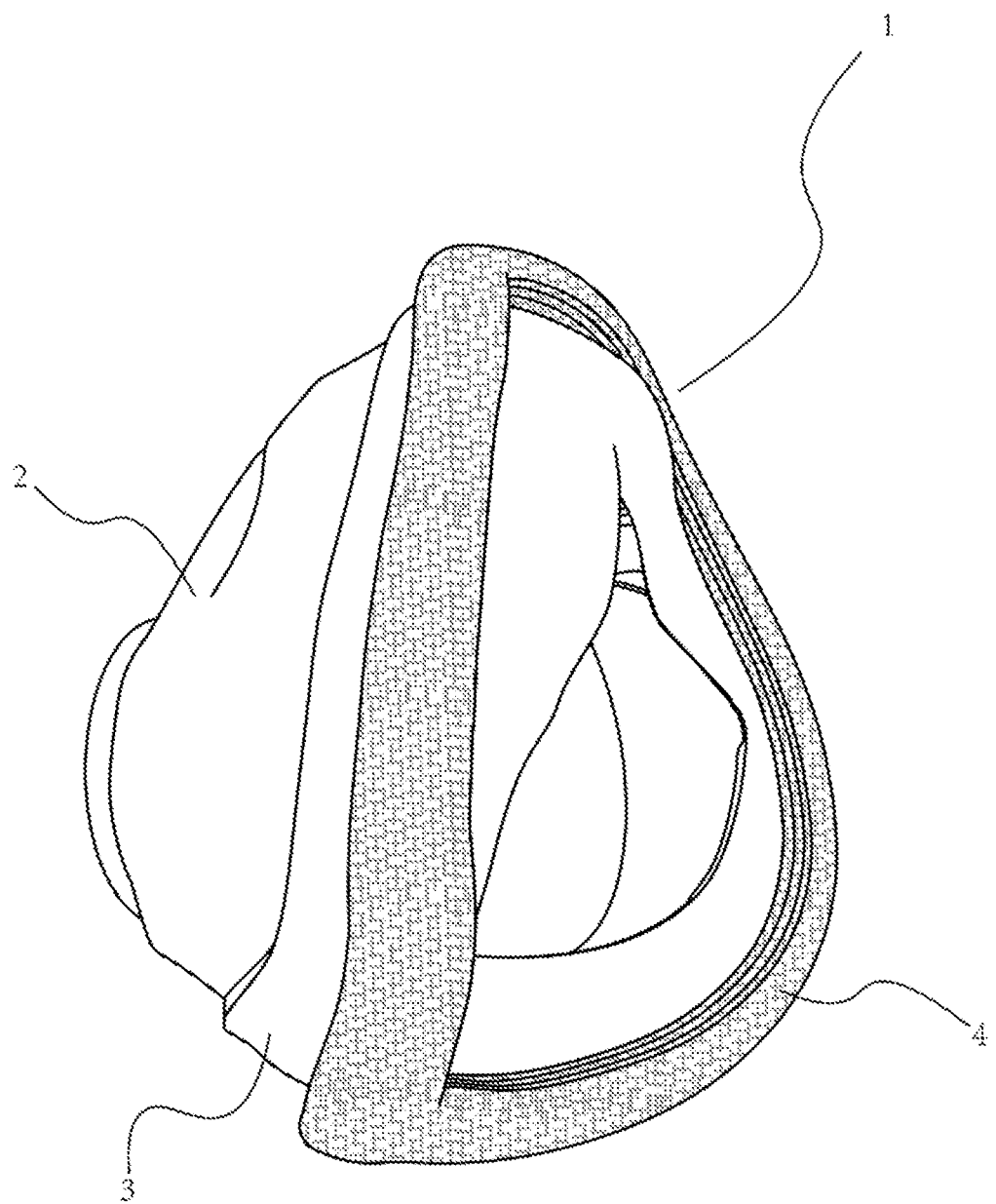
FIG. 14 is a three-dimensional schematic view of a respiratory mask according to an embodiment.

In this embodiment, the respiratory mask has good sealing performance. It is configured to enclose a user's nose and mouth by forming a sealing area between a lower lip and a nasal bridge, or to enclose only the user's nose by forming a sealing area between an upper lip area and the nasal bridge area, wherein the respiratory mask is configured to supply pressurized respiratory gas to the user's airway, which includes a rigid component 2, an elastic component 3, and an annular comfort layer 4. The difference between this respiratory mask 1 and the respiratory mask in Embodiment 1 lies in the material of the annular comfort layer 4. As shown in FIG. 14 (which does not show the nasal mask), the annular comfort layer 4 in this embodiment is made of absorbent material, specifically a textile material, which can be nylon, spandex, or polyester. More specifically, the annular comfort layer 4 is made of multiple layers of textile material (two or more layers), each layer being made from a different type of material. By combining multiple layers of textile materials, the performance of the annular comfort layer 4 is enhanced. The bottom layer of the multi-layered textile material, which is in contact with the elastic component 3, can be made of non-breathable fabric to prevent adhesive from penetrating to the first surface 41 of the annular comfort layer 4. In some variations, this bottom layer can also be covered with a non-breathable membrane to achieve the same function of preventing penetration. In an embodiment, 3-layer textile material combination could be used. The layer closest to the user's face could be made of a spandex fabric that is highly elastic, lightweight, and good at moisture absorption. The middle layer could also have good moisture-absorbing properties but might be made of nylon fabric, which, while less comfortable than spandex, can absorb facial oils and sweat. The bottom layer could be made of polyester-added fabric to prevent the penetration of adhesive. In other variations, different types and numbers of fabric layers can be used. Alternatively, the multi-layered textile material can be a blend of the same material. By stacking identical single layers of fabric, the thickness of the comfort layer can be increased, making it softer to the user.

Embodiment 5

In this embodiment, the respiratory mask has good sealing and is configured to enclose a user's nose and mouth by forming a sealing area between a lower lip and a nasal bridge, or to enclose only the user's nose by forming a sealing area between an upper lip area and the nasal bridge area, wherein the respiratory mask is configured to supply pressurized respiratory gas to the user's airway, which includes a rigid component 2, an elastic component 3, and an annular comfort layer 4. The difference between this respiratory mask 1 and the respiratory mask in Embodiment 1 lies in the material of the annular comfort layer 4. In this embodiment, the annular comfort layer 4 is made from a textile material containing Phase Change Material. Phase Change Material can absorb or release heat during phase changes. Endothermic Phase Change Materials absorb heat, while exothermic Phase Change Materials release heat. The phase change is reversible, allowing the temperature of the annular comfort layer 4 to be regulated so that it can maintain a comfortable skin-feel temperature when in contact with the user's face in varying environments.

Figure 15:
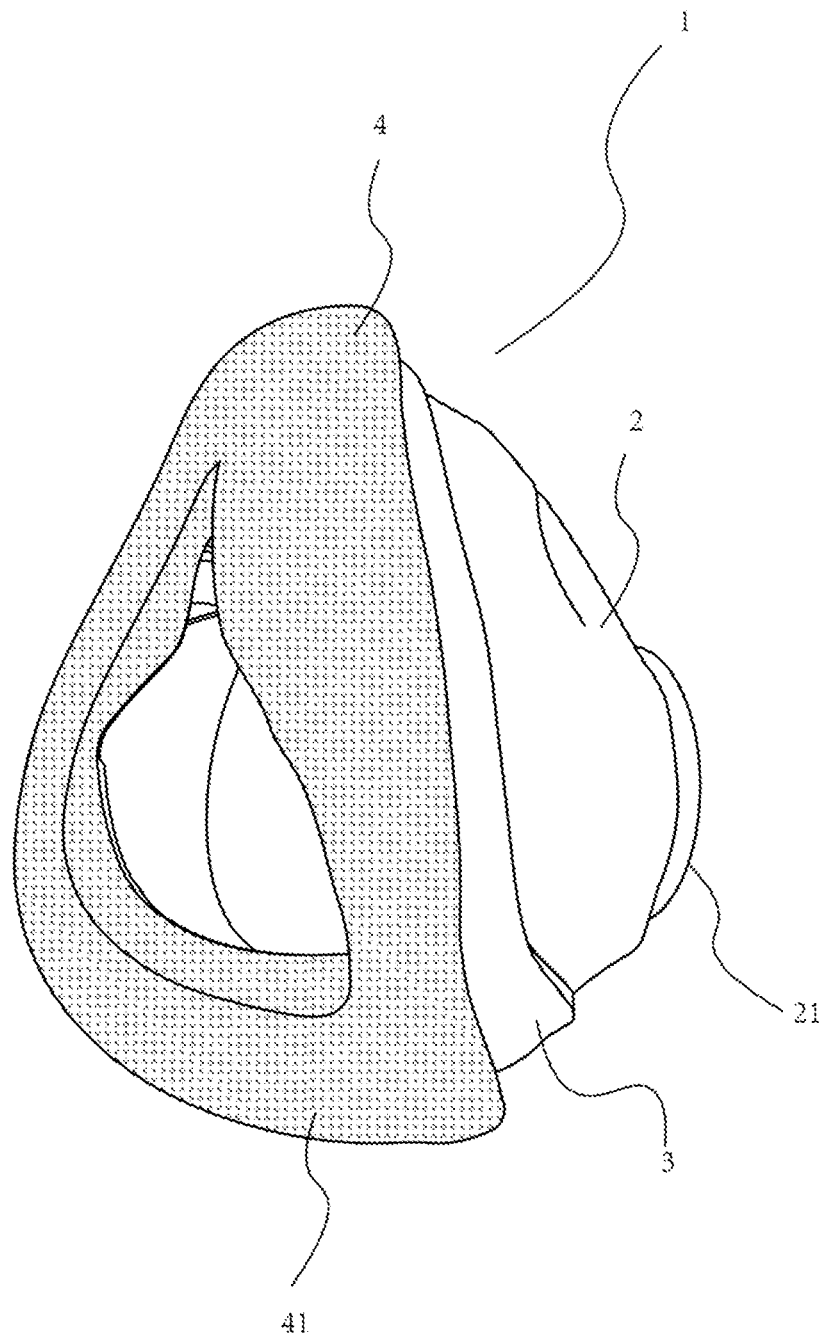
FIG. 15 is a three-dimensional schematic view of a respiratory mask according an embodiment.

In another variation of this embodiment, the annular comfort layer 4 individually contacts the user's face. Here, referring to FIG. 15, the respiratory mask 1 includes a rigid component 2 with at least one gas delivery interface 21 on the side facing away from the user's face. On the side close to the user's face, it features an annular interface with a joint part 22 on its outer edge. The elastic component 3 has a first accommodating area designed to house the user's nose and mouth or only the nose and connects to the inner cavity of the rigid component. The side of the elastic component 3 adjacent to the rigid component is fixedly connected to the joint part 22. The side of the elastic component facing away from the rigid component is used for attaching the annular comfort layer 4. This comfort layer 4 is designed to seal against the user's face during use and includes a second accommodating area that houses the user's nose and mouth and connects to the first accommodating area. It is fixedly attached and covers at least a portion of the side of the elastic component that faces away from the rigid component. This annular comfort layer 4 contains Phase Change Material.

Embodiment 6

This embodiment features a respiratory mask with good sealing configured to enclose a user's nose and mouth by forming a sealing area between a lower lip area and a nasal bridge area, or to enclose only the user's nose by forming a sealing area between an upper lip area and the nasal bridge area, wherein the respiratory mask is configured to supply pressurized respiratory gas to the user's airway, which includes a rigid component 2, an elastic component 3, and an annular comfort layer 4. The difference between this respiratory mask 1 and the respiratory mask in Embodiment 1 lies in the material of the annular comfort layer 4. In this embodiment, the annular comfort layer 4 is made from a composite material containing graphene fibers. Graphene is known for its excellent thermal conductivity, which allows for rapid heat dissipation from the inner part of the annular comfort layer 4, reducing the sensation of stuffiness for the user during use. Moreover, the antibacterial properties of graphene also help reduce bacterial growth during use, keeping the mask clean.

Another variation of this embodiment features the annular comfort layer 4 making direct contact with the user's face. In this case, referring to FIG. 15, the respiratory mask 1 includes rigid component 2 that have at least one gas delivery interface 21 on the side farthest from the user's face. The side closest to the user's face features an annular interface and forms a joint part 22 along the outer edge. The elastic component 3 contains a first accommodation area that houses the user's mouth and nose or only the nose and is connected to the inner cavity of the rigid component. The side of the elastic component 3 closest to the rigid component is fixedly connected to the joint part 22, and the side of the elastic component 3 facing away from the rigid component is used to connect the annular comfort layer 4. The annular comfort layer 4 is configured to seal the user's face during use and includes a second accommodation area for housing the user's mouth and nose or only the nose, which is connected to the first accommodation area. The annular comfort layer 4 is fixedly connected to and at least partially covers the side of the elastic component that faces away from the rigid component, and includes graphene.

Embodiment 7

This embodiment describes a respiratory mask with good sealing configured to enclose a user's nose and mouth by forming a sealing area between a lower lip area and a nasal bridge area, or to enclose only the user's nose by forming a sealing area between an upper lip area and the nasal bridge area, wherein the respiratory mask is configured to supply pressurized respiratory gas to the user's airway, which includes a rigid component 2, an elastic component 3, and an annular comfort layer 4. The difference between this respiratory mask 1 and the respiratory mask in Embodiment 1 lies in the material of the annular comfort layer 4. In this embodiment, the annular comfort layer 4 is made from a composite material infused with antibacterial agents, such as silver chloride or extracts from natural fabrics like tea tree oil, olive leaf extract, or lavender oil. These antibacterial agents effectively inhibit bacterial growth, thereby reducing the risk of infection while using the mask. Additionally, the inclusion of antibacterial agents extends the lifespan of the respiratory mask 1, reducing the frequency with which users need to replace the mask. In some variations, antibacterial fibers, such as silver or copper fibers, can also be added to the annular comfort layer 4 to achieve an antibacterial effect.

In another variation of this embodiment, the annular comfort layer 4 individually contacts the user's face. In this case, referring to FIG. 15, the respiratory mask 1 includes the rigid component 2, which has at least one gas delivery interface 21 on the side farthest from the user's face. On the side of the rigid component 2 closest to the user's face, an annular interface is formed, along with a joint part 22 on the outer edge of the annular interface. The elastic component 3 contains a first accommodation area designed to house the user's mouth and nose or just the nose, and is in communication with the inner cavity of the rigid component. The side of the elastic component 3 closest to the rigid component is fixedly connected to the joint part 22. The side of the elastic component 3 facing away from the rigid component is designed to connect to the annular comfort layer 4. The annular comfort layer 4 is configured to seal against the user's face when in use. This comfort layer has a second accommodation area for housing the user's mouth and nose or just the nose, and it is in communication with the first accommodation area of the elastic component 3. The annular comfort layer 4 is fixedly connected to and covers at least part of the side of the elastic component facing away from the rigid component. This annular comfort layer 4 is made from a composite material that contains antibacterial agents.

Implementing this respiratory mask that is well-sealed and comfortable according to the various embodiments discussed herein include at least the following beneficial effects:

1. The combination of the elastic component 3 and the annular comfort layer 4 allows the respiratory mask 1 to conform to different areas of the face, achieving various degrees of deformation to better fit the facial contours. This results in improved sealing. Additionally, both the elastic component and the annular comfort layer collectively contact the face, evenly distributing the pressure exerted by the tightened straps, reducing red marks or pressure sores, and enhancing comfort.
2. During sleep, the user's head movement, coupled with sweating and oil secretion, can disturb the mask. The annular comfort layer 4 is highly breathable and can absorb sweat and oils, keeping the user's face dry, reducing the likelihood of mask displacement or loss of sealing, and maintaining the mask's effectiveness.
3. Elastic materials are used in the easily damaged nose area, making it more durable and longer-lasting. The annular comfort layer 4 is applied in areas like the cheeks and chin, which are relatively flat and have less variation, making it less prone to tearing. This maximizes both the seal and comfort level while extending the lifespan of the respiratory mask 1.
4. This disclosure innovatively employs a modular design for the face mask. When the rigid component 2 is connected with the elastic component 3, it forms a complete, usable respiratory mask. Notably, the same elastic component 3 can take on two different forms that ensure sealing and therapeutic effects (either with or without the annular comfort layer). Users have the option to install the annular comfort layer 4 based on personal preference. This multifunctional design of a single mask not only saves energy and materials but is also more environmentally friendly.

The above-described embodiments only present several embodiments of the disclosure, which are quite specific and detailed. However, they should not be construed as limitations on the scope of the patent. It should be noted that those skilled in the art could make various modifications and improvements without departing from the concept of this disclosure, and these are within the scope of protection of this disclosure. Therefore, the scope of protection for this patent should be based on the attached claims.

The invention claimed is:
1. A respiratory mask configured to enclose a user's nose and a user's mouth by forming a sealing area between a lower lip and a nasal bridge, or to enclose only the user's nose by forming a sealing area between an upper lip area and the nasal bridge area, wherein the respiratory mask is configured to supply pressurized respiratory gas to an airway of the user, the respiratory mask comprising:
 a rigid component comprising:
  at least one gas delivery interface at a side configured to be farthest away from a face of the user, and
  an annular interface at a nearest side of the rigid component configured to be closest to the face of the user configured to form a joint part along an outer edge of the annular interface;
 an elastic component including:
  a first accommodation area configured to house the user's mouth and the user's nose or only the nose, the first accommodation area communicating with an inner cavity of the rigid component, and the first accommodation area having a side of the elastic component that is closest to the rigid component fixedly connected to the joint part,
  a pressing part configured to seal at least a portion of the user's nose on a side of the elastic component that faces away from the rigid component; and
 an annular comfort layer configured to seal at least part of the face of the user when in use, the annular comfort layer including:
  a second accommodation area configured to house the user's mouth and the user's nose or only the nose, the second accommodation area being connected to the first accommodation area,
   wherein the annular comfort layer is fixedly connected to the side of the elastic component facing away from the rigid component and covers at least part of the pressing part and is configured to form a sealed surface that contacts the face of the user together with the elastic component;
   wherein a portion of the elastic component is configured to contact the face of the user within the interior of an inner edge of the annular comfort layer,
   wherein the annular comfort layer is made of foam material;
   wherein the annular comfort layer is configured to include a density at or between 10 to 200 kg/m$^3$; and wherein the annular comfort layer is configured to include a ratio of a width to a height at or between 0.1 to 30.

2. The respiratory mask according to claim 1, wherein the rigid component is made of plastic material,
the elastic component is made of silicone, rubber, thermoplastic elastomer, or silicone resin material, and
the annular comfort layer is made of polyurethane, low-density polyether, or ethylene-vinyl acetate material.

3. The respiratory mask according to claim 2, wherein a cross-sectional shape of the annular comfort layer is triangular, quadrilateral, pentagonal, or hexagonal.

4. The respiratory mask according to claim 3, wherein a perimeter of an inner edge of the annular comfort layer is greater than or equal to a perimeter of an inner edge on a side of the elastic component adjacent to the pressing part.

5. A respiratory mask configured to enclose a user's nose and a user's mouth by forming a sealing area between a lower lip area and a nasal bridge area, or to enclose only the user's nose by forming a sealing area between an upper lip area and the nasal bridge area, wherein the respiratory mask is configured to supply pressurized respiratory gas to an airway of the user, the respiratory mask comprising:
   a rigid component comprising:
      at least one gas delivery interface at a farthest side configured to be away from a face of the user, and
      an annular interface at a nearest side of the rigid component configured to be closest to the face of the user configured to form a joint part along an outer edge of the annular interface;
   an elastic component including:
      a first accommodation area configured to house the user's mouth and the user's nose or only the nose, the first accommodation area communicating with an inner cavity of the rigid component, and the first accommodation area having a side of the elastic component that is closest to the rigid component fixedly connected to the joint part,
      a pressing part configured to seal at least a portion of the user's nose on a side of the elastic component that faces away from the rigid component, and
   an annular comfort layer configured to seal at least part of the face of the user when in use, the annular comfort layer including:
      a second accommodation area configured to house the user's mouth and the user's nose or only the nose, the second accommodation area being connected to the first accommodation area,
      wherein the annular comfort layer is fixedly connected to the side of the elastic component facing away from the rigid component and covers at least part of the pressing part, and is configured to form a sealed surface that contacts the face of the user together with the elastic component within the interior of an inner edge of the annular comfort layer;
      wherein the annular comfort layer is made of foam material;
      wherein the annular comfort layer includes a first surface configured to be in contact with the face of the user and a second surface connected to the elastic component, with an angle α between the first surface and the second surface being at or between 0 to 80 degrees;
      wherein the annular comfort layer is configured to include a density at or between 10 to 200 kg/m³; and
      wherein the annular comfort layer is configured to include a ratio of a width to a height at or between 0.1 to 30.

6. The respiratory mask according to claim 5, wherein the elastic component is made of silicone material,
the annular comfort layer is made of polyurethane, low-density polyether, or ethylene-vinyl acetate material,
a perimeter of an inner edge of the annular comfort layer is greater than or equal to a perimeter of an inner edge on a side of the elastic component adjacent to the pressing part, and
a shape of the second surface of the annular comfort layer is adapted to a shape on the side adjacent to the pressing part of the elastic component.

7. The respiratory mask according to claim 6, wherein a height of the annular comfort layer is at or between 1 to 30 mm.

8. The respiratory mask according to claim 5, wherein the elastic component and the annular comfort layer are connected through molding, hot pressing, welding, foaming, or adhesive.

9. A respiratory mask configured to enclose a user's nose and mouth by forming a sealing area between a lower lip area and a nasal bridge area, or to enclose only the user's nose by forming a sealing area between an upper lip area and the nasal bridge area, wherein the respiratory mask is configured to supply pressurized respiratory gas to an airway of the user, the respiratory mask comprising:
   a rigid component comprising:
      at least one gas delivery interface at a side configured to be farthest away from a face of the user, and
      an annular interface at a nearest side of the rigid component configured to be closest to the face of the user configured to form a joint part along an outer edge of the annular interface;
   an elastic component, configured to adjust a distance between the rigid component and the face of the user, the elastic component including:
      a first accommodation area configured to house the user's mouth and the user's nose or only the nose, the first accommodation area communicating with an inner cavity of the rigid component, and the first accommodation area having:
         a side of the elastic component closest to the rigid component fixedly connected to the joint part, and
         a side of the elastic component facing away from the rigid component having a non-thin area and at least one thin area, with a wall thickness of the thin area being at or between 0.2 to 2 mm;
   an annular comfort layer configured to seal at least part of the face of the user when in use, a portion of the elastic component being configured to contact the face of the user within the interior of an inner edge of the annular comfort layer, the annular comfort layer including:
      a second accommodation area configured to house the user's mouth and the user's nose or only the nose, the second accommodation area being connected to the first accommodation area,
      wherein the annular comfort layer is fixedly connected to the side of the elastic component that faces away from the rigid component and covers at least part of the elastic component;
      wherein the annular comfort layer made of at least one absorbent material;

wherein the annular comfort layer includes a first surface that is configured to contact the face of the user and a second surface that connects to the elastic component;

wherein the distance variation between the first surface of the annular comfort layer and the rigid component is to yield at least two different values when applying a same force in a constant direction to different positions of the annular comfort layer;

wherein the annular comfort layer is configured to include a density at or between 10 to 200 kg/m³; and wherein the annular comfort layer is configured to include a ratio of a width to a height at or between 0.1 to 30.

10. The respiratory mask according to claim 9, wherein both the thin area and the non-thin area are configured to be at least partially in contact with the face of the user, and the thickness of at least one portion of the thin area configured to contact the face of the user is 7%-60% of a thickness of a portion of the non-thin area configured to contact the face of the user.

11. The respiratory mask according to claim 10, wherein the thin area corresponds to at least one of the user's nose or the user's mouth.

12. The respiratory mask according to claim 9, wherein the elastic component is made of non-breathable material, and the annular comfort layer is made of foam material, textile material, or a composite material of foam and textile, the foam material being polyurethane.

13. A respiratory mask configured to enclose a user's nose and a user's mouth by forming a sealing area between a lower lip area and a nasal bridge area, or to enclose only the user's nose by forming a sealing area between an upper lip area and the nasal bridge area, wherein the respiratory mask is configured to supply pressurized respiratory gas to an airway of the user, the respiratory mask comprising:

a rigid component comprising:
  at least one gas delivery interface at a side configured to be farthest away from a face of the user, and
  an annular interface at a nearest side of the rigid component configured to be closest to the face of the user configured to form a joint part along an outer edge of the annular interface;

an elastic component, configured to adjust a distance between the rigid component and the face of the user, the elastic component including:
  a first accommodation area configured to house the user's mouth and the user's nose, the first accommodation area communicating with an inner cavity of the rigid component, the first accommodation area having:
    a side of the elastic component closest to the rigid component fixedly connected to the joint part, and
    a side of the elastic component facing away from the rigid component having a non-thin area and at least one thin area, with a wall thickness of the thin area being at or between 0.2 to 2 mm; and an annular comfort layer configured to seal at least part of the user's face when in use, the annular comfort layer including:
  a second accommodation area configured to house the user's mouth and the user's nose, the second accommodation area being connected to the first accommodation area,
    wherein the annular comfort layer is fixedly connected to the side of the elastic component facing away from the rigid component and covers at least part of the elastic component to form a sealed surface that contacts the face of the user together with the elastic component;
    wherein the annular comfort layer is made of at least one absorbent material;
    wherein the annular comfort layer includes a first surface that is configured to contact the face of the user and a second surface that is configured to connect to the elastic component, and
    wherein a portion of the elastic component is configured to extend closer to the patient's face than the annular comfort layer.

14. The respiratory mask according to claim 13, wherein an angle α between the first surface and the second surface is at or between 0 to 80°, and the thin area corresponds to at least one of the user's nose or the user's mouth.

15. The respiratory mask according to claim 13, wherein the elastic component is made of silicone, rubber, thermoplastic elastomer, or silicone resin material, and the absorbent material is foam material, textile material, or a composite of foam and textile materials.

16. The respiratory mask according to claim 13, wherein the elastic component and the annular comfort layer are connected in a non-removable manner.

17. The respiratory mask according to claim 13, wherein the elastic component is made of silicone material, the annular comfort layer is made of textile material, which is nylon, spandex, or polyester; and a perimeter of an inner edge of the annular comfort layer is greater than or equal to a perimeter of an inner edge on a side of the elastic component adjacent to a pressing part configured to seal at least a portion of the user's nose thereto.

18. The respiratory mask according to claim 13, wherein a height of the annular comfort layer is uniform.

* * * * *